US012364486B2

(12) United States Patent
Torrie et al.

(10) Patent No.: US 12,364,486 B2
(45) Date of Patent: *Jul. 22, 2025

(54) TISSUE COLLECTION AND DELIVERY DEVICE AND METHODS OF USE THEREOF

(71) Applicant: Smith & Nephew, Inc., Memphis, TN (US)

(72) Inventors: Paul Alexander Torrie, Marblehead, MA (US); Kenneth W. Krause, Sandown, NH (US)

(73) Assignee: SMITH & NEPHEW, INC., Memphis, TN (US)

( * ) Notice: Subject to any disclaimer, the term of this patent is extended or adjusted under 35 U.S.C. 154(b) by 778 days.

This patent is subject to a terminal disclaimer.

(21) Appl. No.: 17/714,558

(22) Filed: Apr. 6, 2022

(65) Prior Publication Data

US 2022/0226005 A1 Jul. 21, 2022

Related U.S. Application Data

(63) Continuation of application No. 16/346,949, filed as application No. PCT/US2019/012870 on Jan. 9, 2019, now Pat. No. 11,324,520.

(60) Provisional application No. 62/622,247, filed on Jan. 26, 2018.

(51) Int. Cl.
| | |
|---|---|
| *A61B 17/16* | (2006.01) |
| *A61B 10/02* | (2006.01) |
| *A61F 2/46* | (2006.01) |
| *A61M 5/31* | (2006.01) |
| *A61M 5/315* | (2006.01) |
| *A61B 17/00* | (2006.01) |
| *C12M 1/33* | (2006.01) |

(52) U.S. Cl.
CPC ...... *A61B 17/1635* (2013.01); *A61B 10/0233* (2013.01); *A61F 2/4601* (2013.01); *A61M 5/3145* (2013.01); *A61M 5/31596* (2013.01); *A61B 2017/00398* (2013.01); *A61B 2017/00969* (2013.01); *A61B 2217/005* (2013.01); *A61M 2202/09* (2013.01); *C12M 45/02* (2013.01)

(58) Field of Classification Search
CPC ............ A61B 17/1635; A61B 10/0233; A61B 2017/00398; A61B 2017/00969; A61B 2217/005; A61B 17/1615; A61B 17/162; A61B 17/1622; A61B 17/1631; A61B 17/1646; A61B 2017/00464; A61F 2/4601; A61M 5/3145; A61M 5/31596; A61M 2202/09; C12M 45/02

See application file for complete search history.

(56) References Cited

U.S. PATENT DOCUMENTS

| | | | |
|---|---|---|---|
| 10,639,046 B2* | 5/2020 | Torrie | A61B 17/1635 |
| 10,687,827 B1* | 6/2020 | Torrie | A61B 10/0233 |
| 2008/0234715 A1* | 9/2008 | Pesce | A61B 17/32002 606/171 |
| 2018/0344327 A1* | 12/2018 | Jeng | A61B 17/1635 |

* cited by examiner

*Primary Examiner* — Theodore J Stigell
(74) *Attorney, Agent, or Firm* — ArentFox Schiff LLP; Joseph M. Maraia; Marlo Schepper Grolnic

(57) ABSTRACT

A system and method for harvesting autologous tissue, mincing it into fragments that are visible and measurable when filtered, and delivering a portion of the tissue back into the patient without the need to directly touch the tissue. During the same surgical procedure, the tissue can be mixed with a biocompatible agent before introduction into the repair site.

16 Claims, 17 Drawing Sheets

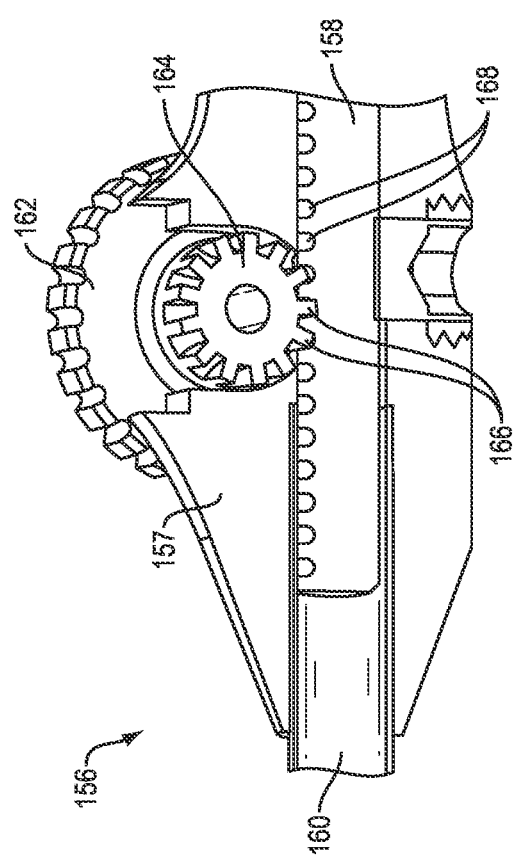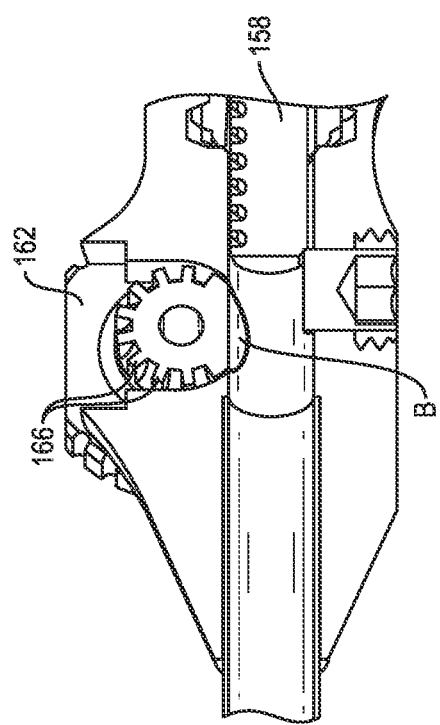

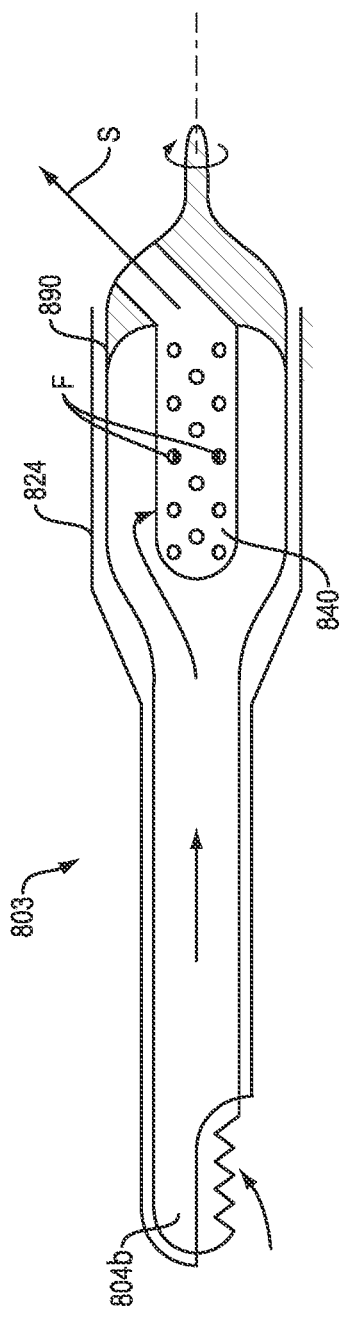
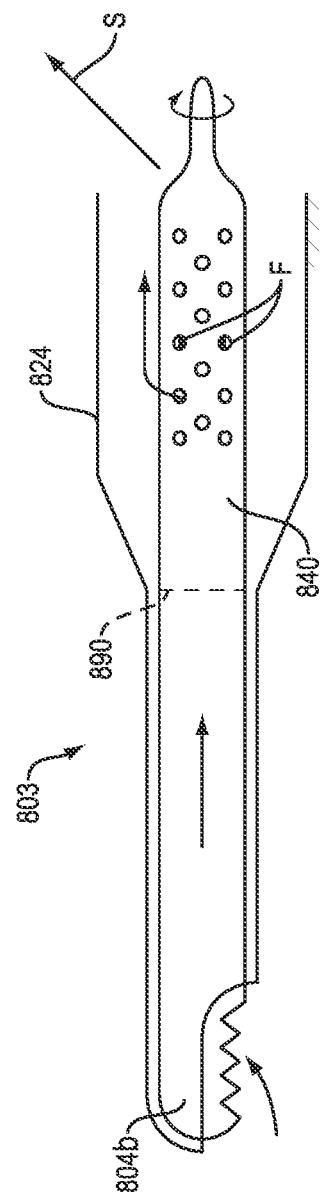

TISSUE COLLECTION AND DELIVERY DEVICE AND METHODS OF USE THEREOF

CROSS-REFERENCE TO RELATED APPLICATIONS

This application is a continuation of co-pending U.S. application Ser. No. 16/346,949, entitled TISSUE COLLECTION AND DELIVERY DEVICE AND METHODS OF USE THEREOF, which in turn is the U.S. national phase entry under 35 U.S.C. § 371 of International Application No. PCT/US2019/012870, filed Jan. 9, 2019, which in turn claims priority to and benefit of U.S. Provisional Application No. 62/622,247, filed Jan. 26, 2018, the contents of which are incorporated herein by reference in their entirety for all purposes.

TECHNICAL FIELD

The present disclosure relates generally to tissue harvesting and, more particularly, to a device for collecting autologous tissue from a surgical site and delivering the collected material where desired.

BACKGROUND

Articular cartilage is an avascular tissue which lines the ends of the bones and facilitates frictionless movement of the joints, such as the knee joint. Damage to cartilage caused by injury or disease does not heal on its own, and the pathological changes resulting from this damage can be a source of pain and limited mobility to a patient, and can have a significant detrimental impact on the patient's quality of life. Additionally, over time, cartilage lesions are likely to degenerate into osteoarthritis and the need for a total joint replacement.

In some cases, tissue harvesting techniques can be used to treat cartilage lesions and postpone or obviate the need for a joint replacement. These techniques enable a surgeon to purify a unique population of repair cells from the patient's tissues, such as synovial or adipose tissue, and deliver the cells back into the patient's joint to stimulate cartilage repair. The repair cells are harvested arthroscopically from a site local to the defect (i.e. within the joint), and repair cells of a desired size are isolated, for example, by filtering. The isolated cells are typically mixed with a biocompatible "gluing" agent and the mixture of the agent and the harvested cells is then provided to the repair site. The use of autologous tissue is particularly desirable as it substantially reduces the potential for an immunogenic host response and tissue rejection.

Various tissue harvesting techniques for treating cartilage are known in the art. Some examples include mosaicplasty, in which plugs of cartilage and bone are harvested from low weight-bearing regions of the joint and transplanted into the defect; or autologous chondrocyte implantation (ACI), in which cells are isolated and expanded from a cartilage biopsy and re-introduced into the defect in a second procedure. However, some of these techniques, like ACI, involve separate surgical procedures that occur on two different days, which may be weeks apart. Even for single surgery techniques, clinical results suggest that the long-term biochemical and biomechanical properties of the reparative tissue are generally not ideal.

SUMMARY

Described herein are low cost, simple, one-surgery systems and methods for harvesting autologous tissues from a patient and delivering them into another area that requires repair. The system of this disclosure harvests autologous tissue, minces it into fragments that are visible and measureable when filtered, and delivers a portion of the tissue back into the patient. Advantageously, this is accomplished without the need to directly touch the tissue, thus eliminating the risk of disease transmission and immune response associated with such treatment. During the same surgical procedure, the isolated cut tissue can be loaded into, or mixed with, an appropriate carrier before introduction into the repair site. The systems and methods of this disclosure advantageously reduce the need for multiple surgeries and also facilitate improved long-term recovery outcomes by efficiently harvesting and implanting autologous tissue during a single surgical procedure.

Further examples of the systems and methods of this disclosure may include one or more of the following, in any suitable combination.

In examples, the tissue collection assembly of this disclosure includes a resection system having a handpiece with a proximal end, a distal end, and a passageway therethrough. The resection system also includes a cannulated shaft attached to the handpiece in fluid communication with the passageway. A distal end of the shaft has a cutting end. The tissue collection assembly also includes a filter assembly removeably attached to the handpiece in fluid communication with the cannulated shaft. The filter assembly includes a housing allowing direct visualization of an internal volume of the housing, a filter removeably disposed within the internal volume of the housing for collecting tissue on a surface of the filter, and a compressor extendable through the internal volume of the housing for compressing the collected tissue. The filter assembly is coupleable with a delivery device to deliver the collected tissue to a repair site.

In other examples, the handpiece further includes rigid tubing and a barb in fluid communication with the filter assembly. The compressor has an inlet for removeable attachment to the barb. The housing also includes a removeable outlet for attachment to a vacuum source. The filter is coupled to the outlet such that the filter and the outlet are removeable from the housing simultaneously. In examples, the housing further includes a shearing member slidably disposed around the filter for removing the collected tissue from the filter. In examples, the resection system also includes a flexible shield adjacent the cutting end of the shaft. In examples, the handpiece is a motorized drive unit having at least one internal structure to prevent contamination of the collected tissue by the handpiece. In examples, the at least one internal structure is a flow diverter or a sleeve integrated with the passageway of the handpiece. In further examples, the tissue collection assembly includes one or more deformable wires for mixing the collected tissue with a biocompatible agent. The wires are attached to the compressor or to the plunger. In examples, the filter is a hollow, tubular filter, and the surface of the filter comprises holes in communication with an interior of the filter.

Examples of the tissue collection assembly and delivery device combination of this disclosure include a tissue collection assembly with a resection system having a handpiece with a proximal end, a distal end, and a passageway therethrough. The resection system also includes a cannulated shaft attached to the handpiece in fluid communication with the passageway. A distal end of the shaft has a cutting end. The tissue collection assembly also includes a filter assembly removeably attached to the handpiece in fluid communication with the cannulated shaft. The filter assembly includes a housing allowing direct visualization of an internal volume of the housing, a filter removeably disposed within the internal volume of the housing for collecting tissue on a surface of the filter, and a compressor extendable through the internal volume of the housing for compressing the collected tissue. A delivery device is coupleable to a coupling portion of the housing for delivering the collected tissue to a repair site. In further examples, the combination includes a plunger insertable through the compressor and a channel of the delivery device. The combination also includes an actuator for advancing the plunger within the channel and a mechanism for controlling the relative motion between the compressor and the plunger through a portion of the housing. The mechanism is configured to prevent the advancement of the plunger through the housing until the compressor is stopped from advancing through the housing.

Examples of the method of collecting and delivering tissue to a repair site of this disclosure include contacting a blade of a tissue collection assembly with tissue and cutting the tissue with a cutting end of the blade to create tissue fragments. The method also includes aspirating fluid and the tissue fragments through the blade to a filter assembly. The filter assembly includes a housing allowing direct visualization of an internal volume of the housing, the housing in fluid communication with the blade, a filter removeably disposed within the internal volume of the housing for collecting the tissue fragments on a surface of the filter, a compressor extendable through the internal volume of the housing for compressing the tissue fragments, and a shearing member slidably disposed around the filter for removing the collected tissue from the filter. The method also includes separating the tissue fragments having a pre-selected size from the fluid using the filter and detaching the filter assembly from the blade. In examples, the method also includes removing the filter from housing, thereby causing the shearing member to shear the tissue fragments from the surface of the filter, and coupling the filter assembly to a delivery device. Finally, examples of the method include inserting a plunger through the filter assembly and the delivery device to deliver the tissue fragments to a repair site.

Further examples of the method include extending the compressor within the housing to compress the tissue fragments such that a volume of the tissue fragments is measureable by direct visualization. In examples, the method also includes injecting a biocompatible agent into the housing and rotating one or more deformable wires attached to the compressor or the plunger to mix the tissue fragments and the agent. In examples, the method also includes actuating an actuator on the delivery device to advance the plunger within a channel of the delivery device.

Other examples of a resection system of this disclosure include a handpiece having a proximal end, a distal end, and a passageway therethrough. Examples of the resection system also have a cannulated shaft attached to the handpiece in fluid communication with the passageway. A distal end of the shaft has a cutting end. In examples, the resection system also includes a filter removeably disposed within the shaft between the handpiece and the cutting end for collecting tissue on a surface of the filter.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein:

FIGS. 8A and 8B are detailed views of an actuator and plunger interface of the device of FIG. 7B;

FIGS. 14A and 14B illustrate another example of the filter of FIG. 4A; and

DETAILED DESCRIPTION

Figure 1:
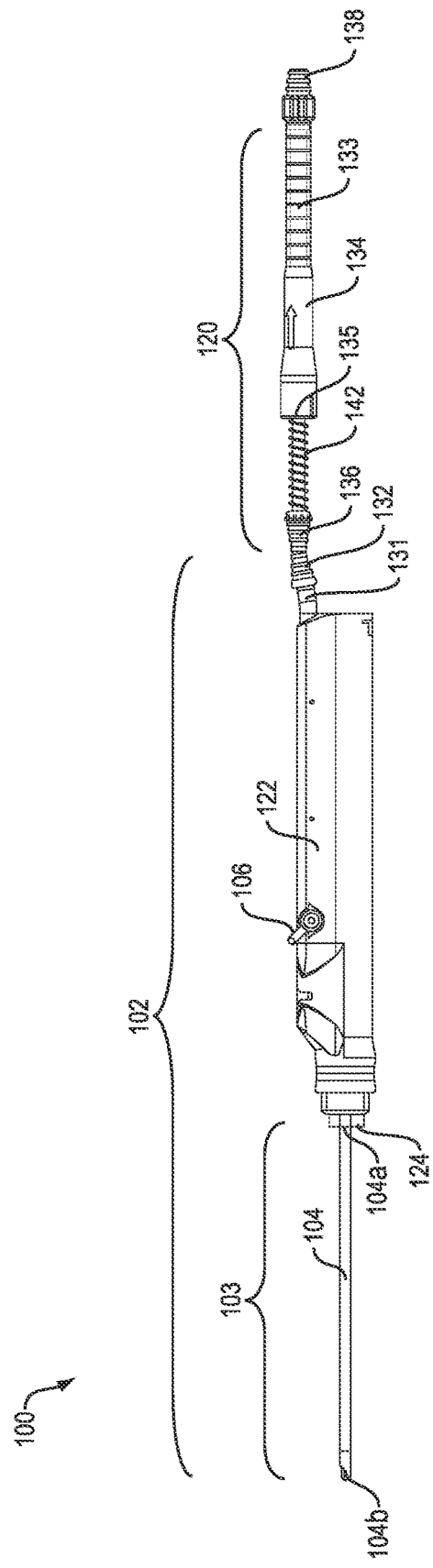
FIG. 1 illustrates an exemplary tissue collection assembly of this disclosure.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Referring now to FIG. 1, an example of a tissue collection assembly 100 of this disclosure is shown in an assembled view. The assembly 100 generally comprises a surgical resection system 102 used to cut or resect bodily tissue from a donor site. Alternatively, other cutting instruments, such as a burr (not shown), may be used. The resection system 102 is in fluid communication with a filter assembly 120 for isolating the tissue fragments which have been aspirated through the resection system 102. Notably, while this disclosure relates primarily to cartilage repair, the tissue collection assembly 100 of this disclosure can be used for harvesting various autologous tissue types (e.g., cartilage, bone, fat, meniscus, tendon, ligament, etc.) in a range of surgical or cosmetic applications.

Still referring to FIG. 1, the resection system 102 includes a surgical blade 103 comprising a cannulated shaft 104, and a handpiece 122 coupled to the shaft 104 via a hub 124. The shaft 104 has a proximal end 104a coupled to the hub 124 and a distal end defining a cutting end 104b. The handpiece 122 provides a pathway for fluid and tissue fragments to flow from the cutting end 104b of the shaft 104 to the filter assembly 120. In examples, the handpiece 122 is a motorized drive unit including a suction lever 106 to control the flow of the tissue fragments through the handpiece 122. In examples, the handpiece 122 includes a rigid tube 131 with a barb 132 in fluid communication with the filter assembly 120.

The filter assembly 120 comprises a substantially cylindrical housing 134 with an outlet 138 removeably attached to the housing 134 for connecting the housing 134 to a vacuum source (not shown). In examples, the vacuum source is a vacuum pump or other suitable apparatus for providing aspiration during the surgical procedure. An inlet 136 is formed integrally with a compressor 142 which at least partially extends through a port 135 in the housing 134. The inlet 136 is configured to be removeably coupled to the barb 132. In examples, the inlet 136 and the barb 132 are connected by flexible tubing (not shown). The inlet 136 and the body of the compressor 142 are configured to axially slide within the internal volume 133 of the housing toward the outlet 138. Thus, a diameter of the port 135 is selected to accommodate the passing of both of the inlet 136 and the compressor 142 through at least a portion of the housing 134.

Figure 2B:
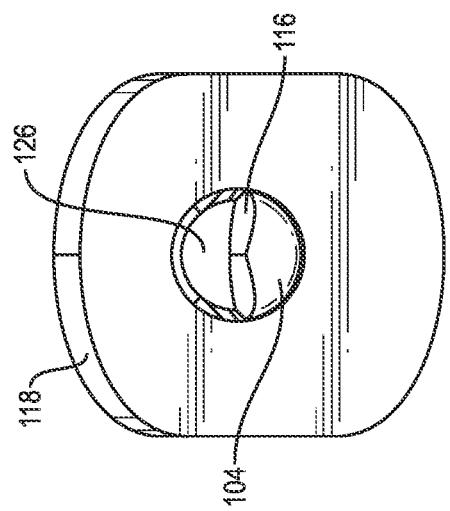
FIGS. 2A and 2B are detailed views of the cutting end of the tissue collection assembly of FIG. 1.
Figure 2A:
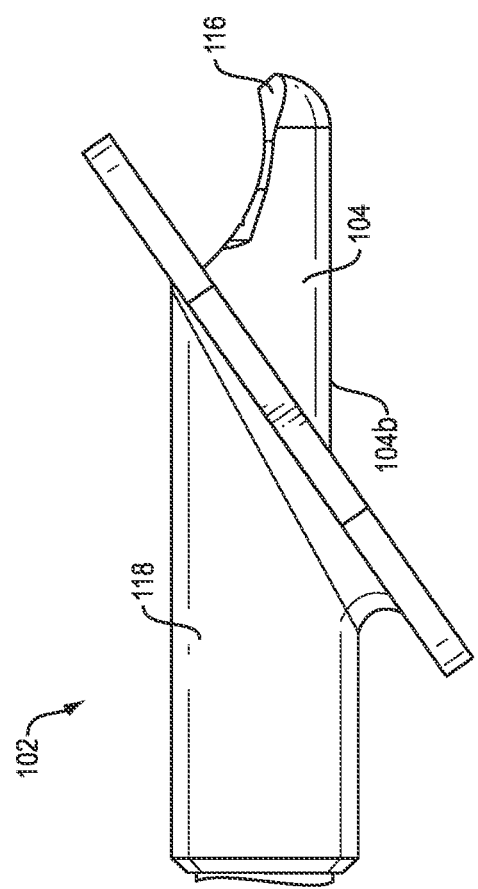

The cutting end 104b of the shaft 104 is shown in greater detail in FIGS. 2A and 2B. As illustrated in FIG. 2A, the cutting end 104b of the shaft 104 includes a cutting edge 116 for fragmenting soft tissue or bone. The shaft 104 furthermore defines an aspiration lumen 126 (FIG. 2B) communicating with the cutting edge 116 to remove the fragmented tissue and fluid from the surgical site. In examples, the cutting end 104b of the shaft 104 includes an external shield 118 removeably disposed around the shaft 104 adjacent to the cutting edge 116. The shield 118 is configured to minimize the amount of foreign material being sucked into the lumen 126. Preferably, the shield 118 is an elastomeric shield that minimizes ingestion of material which is not directly in front of the lumen 126. Advantageously, the pliable nature of the shield 118 minimizes interference with the mobility of the shaft 104 during use.

Figure 3A:
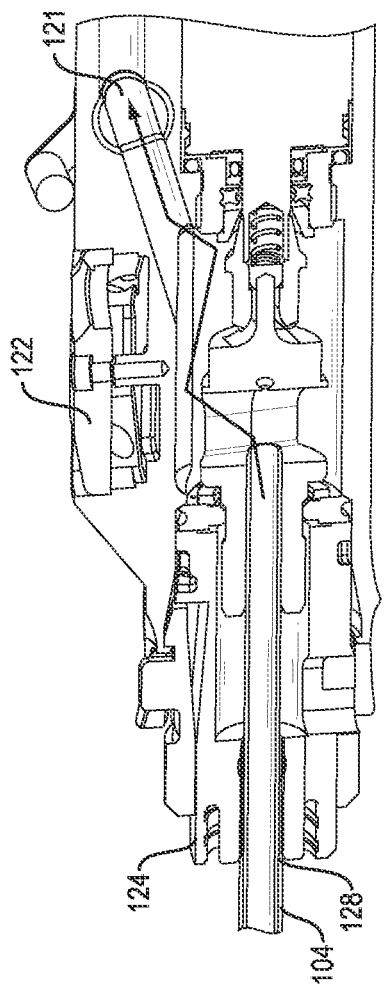
FIGS. 3A-G are detailed views of various examples of the handpiece and blade of the tissue collection assembly of FIG. 1.
Figure 3B:
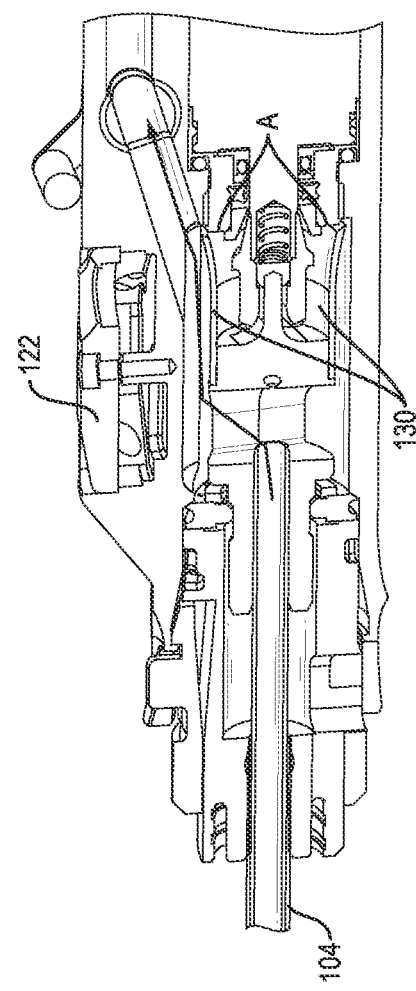
Figure 3C:
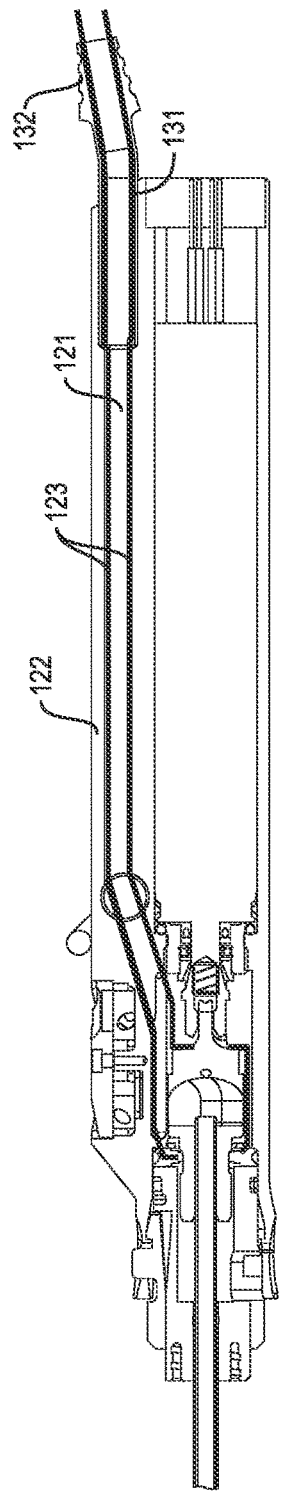

Turning now to FIG. 3A, an exemplary handpiece 122 of this disclosure is illustrated in a cross-sectional view. In FIG. 3A, it can be seen that the hub 124 of the resection system 102 is coupled to the shaft 104 via an opening 128 formed in the hub 124. The handpiece 122 may also include various internal shielding structures to mitigate contamination of the tissue fragments as they travel along a passageway 121 extending through the handpiece 122. For example, the handpiece 122 may include a flow diverter 130 (FIG. 3B) which causes the tissue fragments to bypass the most commonly contaminated areas A of the handpiece 122. In an alternative example, illustrated in FIG. 3C, a sterile sleeve 123 may be integrated within the passageway 121 to prevent contamination of the tissue fragments by the handpiece 122. In examples, the sterile sleeve 123 is made of a thermally-conductive material which is also selected to be deformable, collapse-resistant and shear-resistant through the rigid tubing 131 and the barb 132.

Figure 3E:
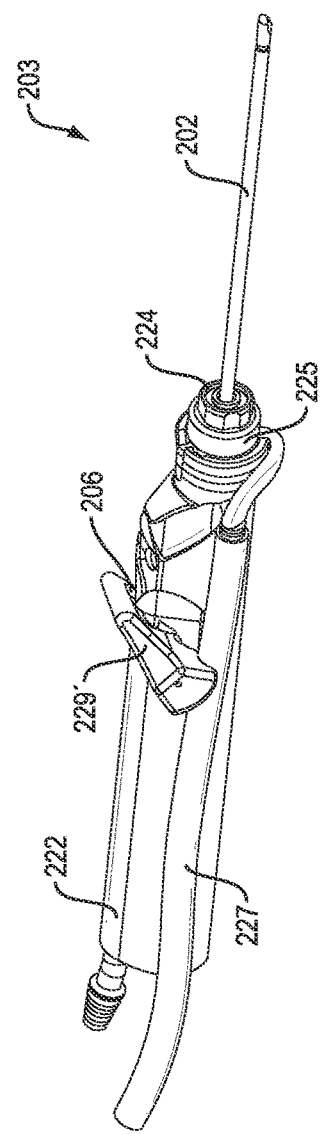
Figure 3D:
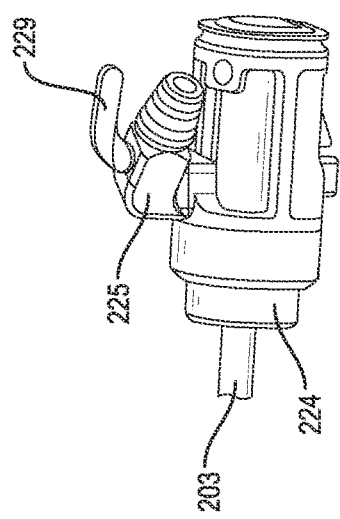
Figure 3F:
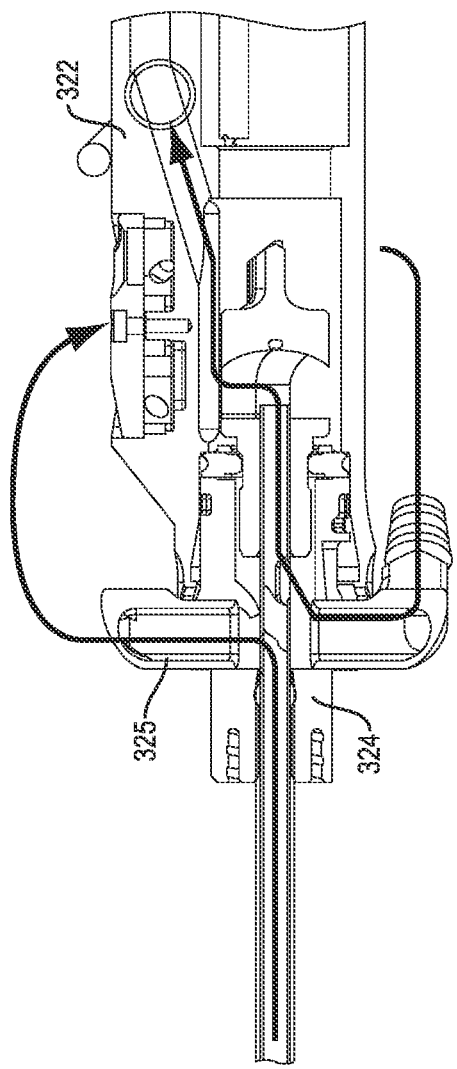
Figure 3G:
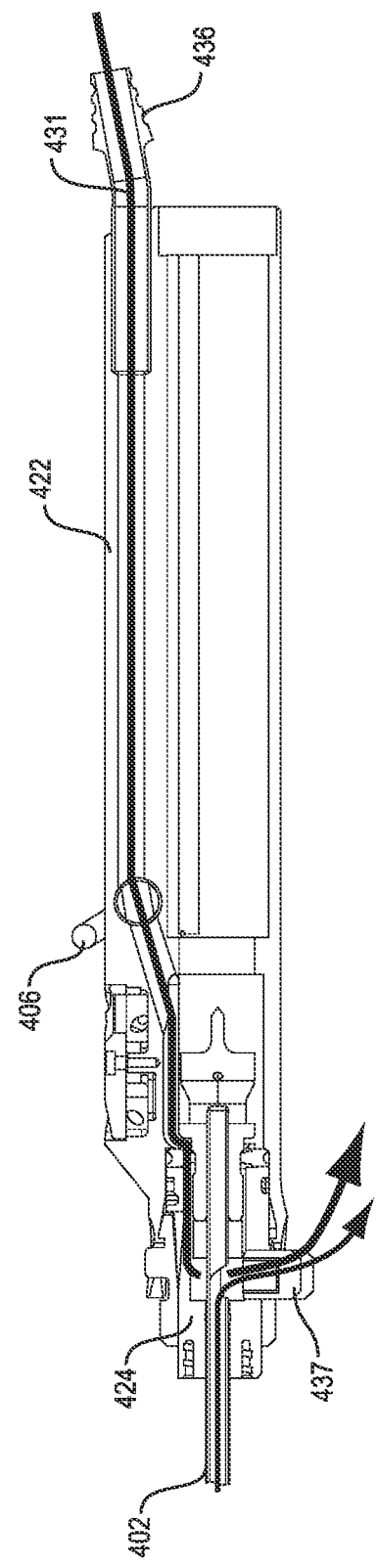

Alternative examples of the handpiece 122 are shown with regard to FIGS. 3D and 3E. In the example shown in FIG. 3D, the tissue fragments could be diverted to flow outside of the blade 203. For example, an outflow port 225 could be integrated on the hub 224 of the blade 203 and connected with tubing 227 (FIG. 3E) which is attached to the filter assembly 120. An integral valve 229 (FIG. 3D) or separate valve 229' attached to the suction lever 206 of the handpiece 222 (FIG. 3E) could be used to control suction. Additionally, a small portion of aspirated fluid could be diverted from the hub 224 to cool down the handpiece 222. In another example, illustrated in FIG. 3F, to fully cool down the handpiece 322, aspirated fluid flowing through the outflow port 325 on the hub 324 could be fed through a filter (not shown) and then back into the hub 324, and then finally through the handpiece 322. In yet another example, shown in FIG. 3G, the suction lever 406 of the handpiece 422 may utilize ambient air 431 to control the suction of the blade 402 when two suction ports or inlets 436, 437 are present. The suction lever 406 on the handpiece 422 controls the air 431 running backwards into the hub 424, thus reducing the effective suction strength of the blade 402.

Figure 4A:
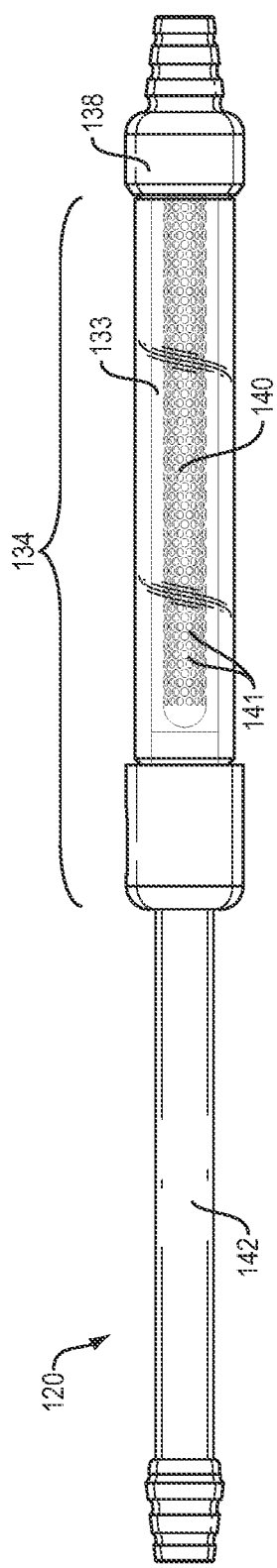
FIGS. 4A and 4B are detailed views of an exemplary filter assembly of the tissue collection assembly of FIG. 1.

Turning now to FIG. 4A, an example of the filter assembly 120 of this disclosure is illustrated in more detail. A filter 140 is disposed within the internal volume 133 of the housing 134 for the collection of tissue fragments about an outer surface of the filter 140. In examples, the filter 140 is a hollow, tubular filter allowing suction to be applied through the interior of the filter 140. However, other suitable filters having any number of possible geometric shapes may be employed. As suction is applied, fluid flows through holes 141 in communication with the interior of the filter 140, causing the tissue fragments to be collected about the outer surface of the filter 140. In examples, a size of the holes 141 is selected to be smaller than a pre-selected size of the tissue fragments.

Figure 4B:
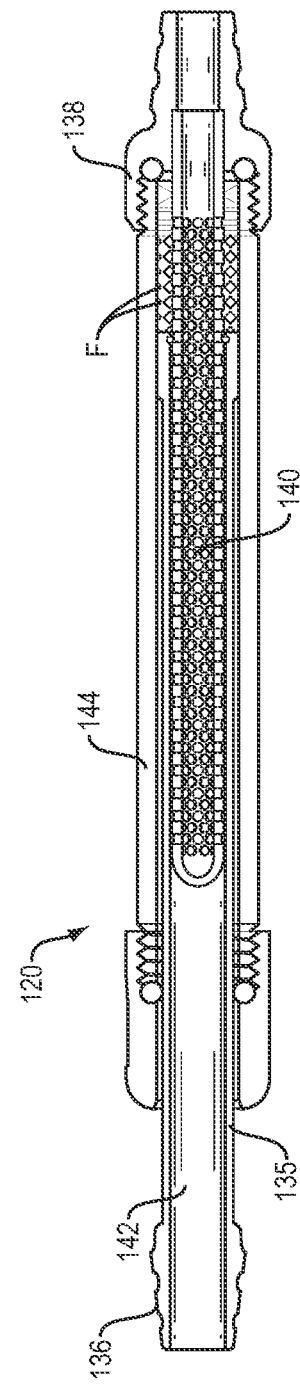

As shown in FIG. 4B, the filter 140 is coupled to the outlet 138 such that the filter 140 and the outlet 138 are removeable from the housing 134 simultaneously. As stated above, the compressor 142 is extendable through a port 135 in the housing and configured to axially slide at least partially within the housing 134 toward the outlet 138. In examples, the compressor 142 may slide within the housing 134 by a manual force exerted on a surface of the compressor 142. Alternatively, closing off the inlet 136 while suction is applied to the filter assembly 120 may act as a force on the surface of the compressor 142, causing the compressor 142 to advance toward to the outlet 138. As the compressor 142 is moved toward the outlet 138, tissue fragments F collected within the housing 134 are compacted against outlet 138, thus allowing measurement of the volume of tissue fragments F harvested. To facilitate this, a portion of the housing 134 may be provided with a transparent surface 144 to allow direct visualization of the tissue fragments F. Furthermore, the transparent surface 144 may include markings 148 (FIG. 5B) to aid in the measurement of the volume of the tissue fragments F. If more tissue fragments are required, additional aspiration could be applied. Notably, during aspiration of the tissue fragments F, a gap must be maintained between the compressor 142 and the filter 140 so that the compressor 140 does not block the collection of the tissue fragments about the filter 140. In examples, a biasing member, such as a spring 143 (FIG. 7A) may be provided to return the compressor 140 back to its initial position away from the filter 140 when the measurement of the tissue fragments F is complete.

Figure 5A:
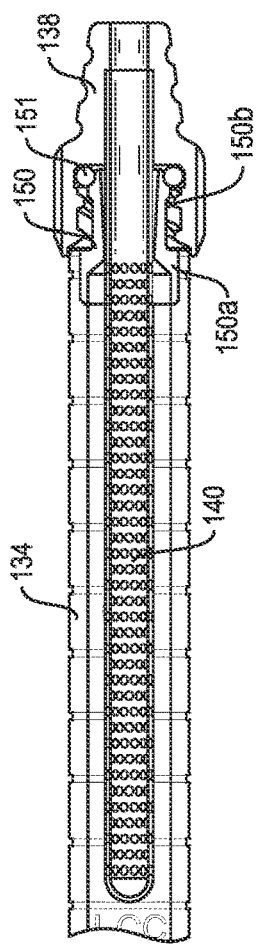
FIGS. 5A-C illustrate removal of the filter from the filter assembly of FIG. 4A.
Figure 5B:
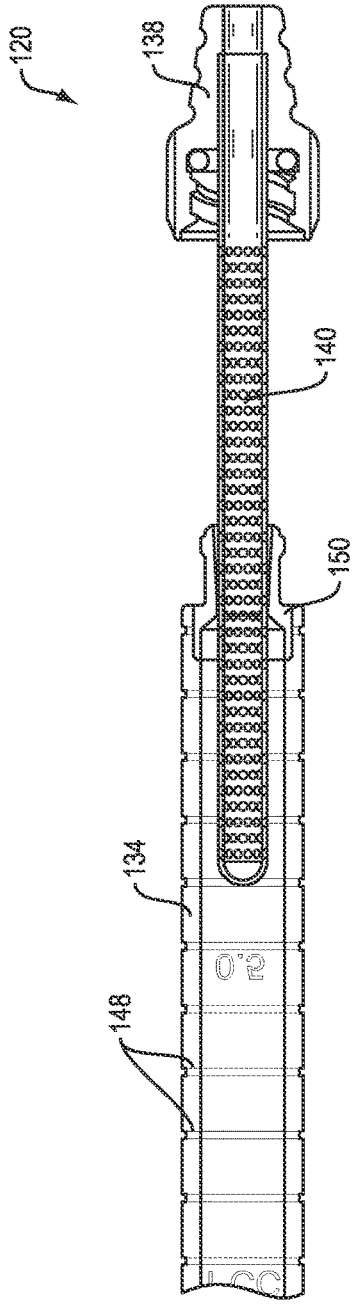
Figure 5C:
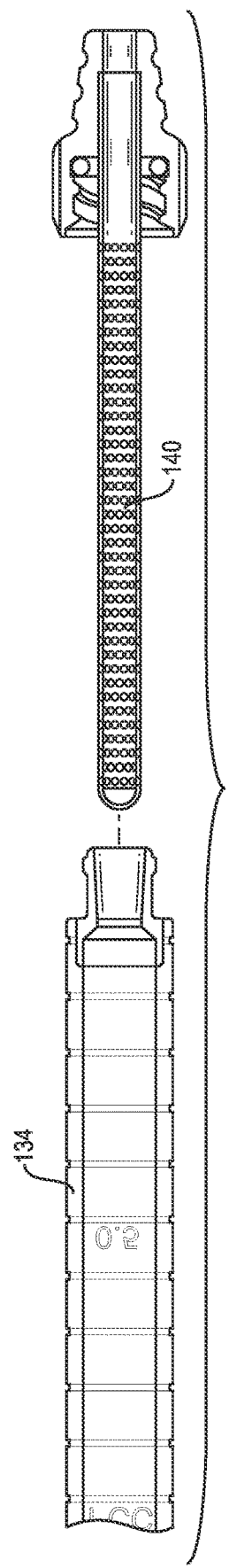

Turning now to FIG. 5A, examples of the housing 134 of this disclosure may include a shearing lip 150 at the proximal end of the housing 134 and slidably disposed about a portion of the filter 140. A first portion 150a of the lip 150 is fixedly disposed within the housing 134 and a second portion 150b of the lip 150 is removeably disposed within a cavity 151 of the outlet 138. Thus, the outlet 138 and the filter 140 may be removed from the housing 134 without changing the position of the lip 150 relative to the housing 134. As the outlet 138 and the filter 140 are removed from the housing 134 (FIG. 5B), the lip 150 acts to shear the tissue fragments off of the outer surface of the filter 140, thus leaving the tissue fragments within the filter assembly 120 and ready for delivery to a repair site. After removal of the filter 140 (FIG. 5C), a biocompatible agent may be introduced into the housing 134 to facilitate the attachment of the fragments to the repair site after delivery. The agent may comprise any suitable biological or synthetic agent. For example, the agent may comprise hyaluronic acid, alginate, cross-linked alginate, collagen, fibrin glue, fibrin clot, poly (N-isopropulacrylamide), agarose, chitin, chitosan, cellulose, polysaccharides, poly(oxyalkylene), a copolymer of poly(ethylene oxide)-poly(propylene oxide), poly(vinyl alcohol), polyacrylate, Matrigel, or mixtures thereof.

Figure 6A:
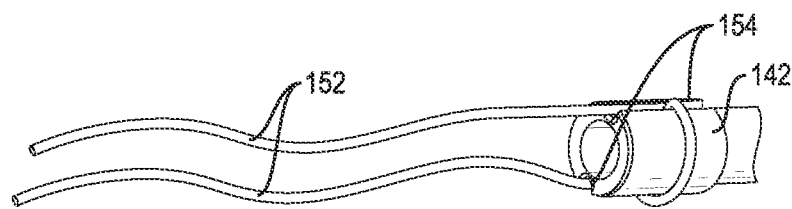
FIGS. 6A-C are detailed views of exemplary mixing elements of the tissue collection assembly of FIG. 1.
Figure 6B:
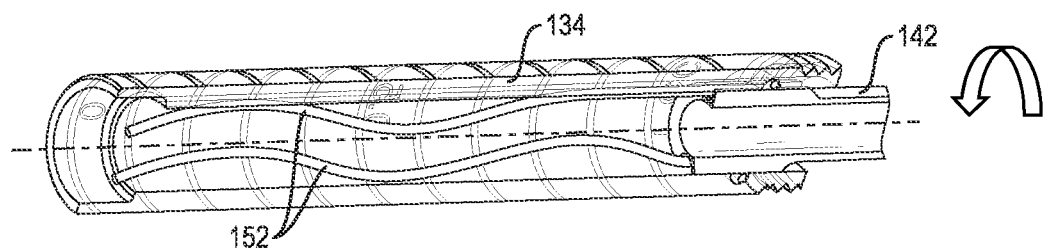
Figure 6C:
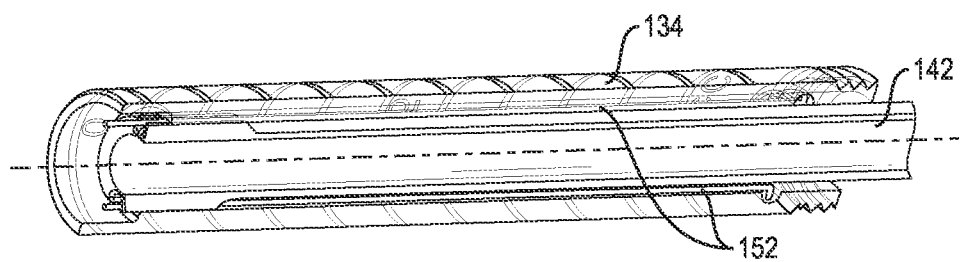

As shown in FIG. 6A, examples of the compressor 142 of this disclosure may further include one or more asymmetrical wires 152 attached to the compressor 142. For example, the wires 152 may be slidably received within grooves 154 on an outer surface of the compressor 142. The wires 152 may be used for mixing the collected tissue fragments with the introduced agent. Rotary motion is transferred to the wires 152 by rotation of the compressor 142 relative to the housing 134 to create a mixture of agent and tissue fragments within the housing 134 (FIG. 6B). Notably, the wires 152 may be made of a deformable material such that the wires 152 do not impede axial movement of the compressor 142 through the housing 134 (FIG. 6C).

Figure 7A:
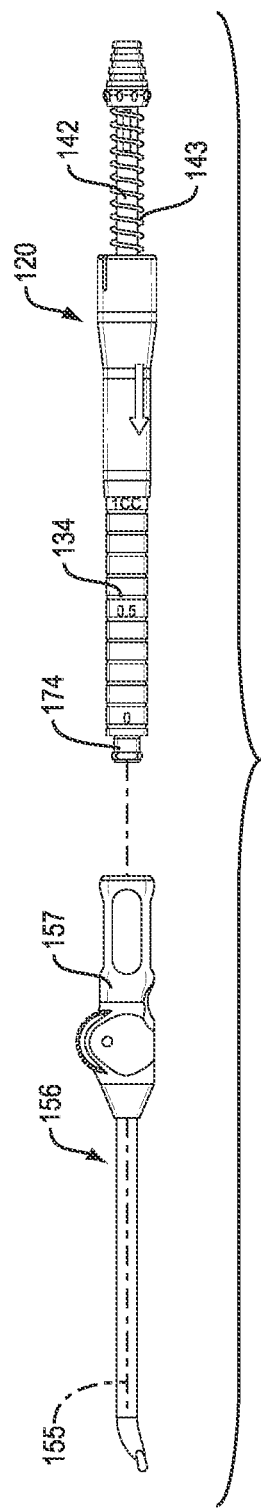
FIGS. 7A and 7B illustrate an exemplary tissue collection and delivery device of this disclosure in an exploded view (FIG. 7A) and an assembled view (FIG. 7B)
Figure 7B:
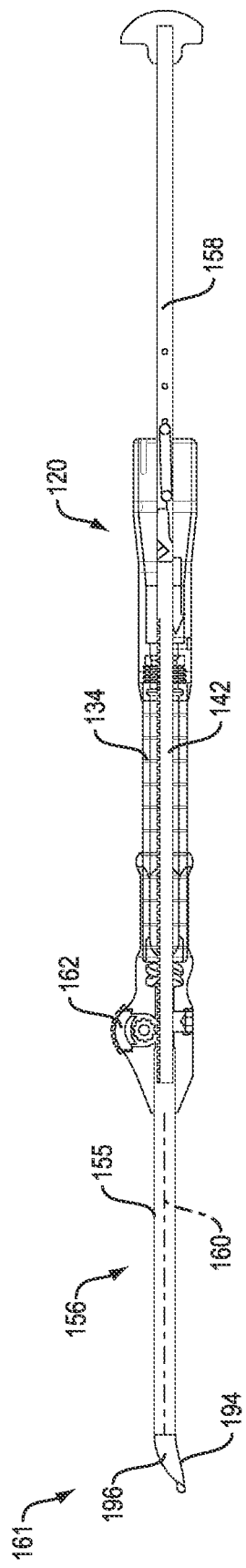
Figure 7C:
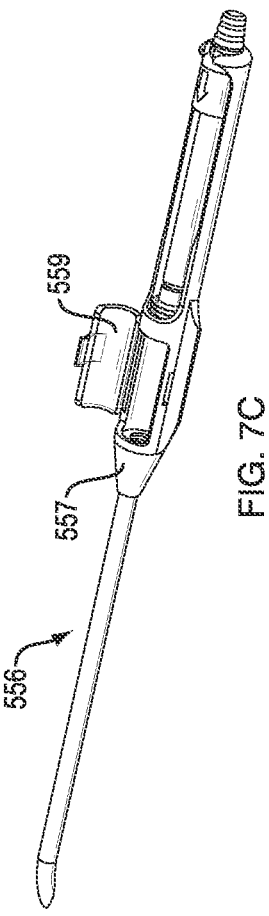
FIG. 7C illustrates an alternative example of the delivery device of FIG. 7A.

Turning now to FIG. 7A, an example of a delivery device 156 used to deliver the tissue fragments collected in the filter assembly 120 is shown. The delivery device 156 generally comprises a cannulated shaft 155 and a handle 157. The handle 157 is configured to mate with a coupling portion 174 of the housing 134 (for example, a Luer or threaded fitting) of the filter assembly 120, as shown in FIG. 7B. A channel 160 extending through the shaft 155 and the handle 157 of the delivery device 156 is configured for the passage of a plunger 158 inserted through the inlet 136 of the compressor 142 to deliver the tissue fragments out of a delivery end 161 of the shaft 155. In examples, a diameter of the channel 160 is selected to minimize resistance of the tissue fragments as the plunger 158 is advanced through the channel 160. A lip 196 surrounds at least a portion of the circumference of the delivery end 161 of the shaft 155 and extends a distance radially from the shaft 155. A surface of the lip 196 is aligned with a portion of an opening 194 of the shaft 155, the surface being substantially planar. This configuration allows the lip 196 to be dragged over the repair site during tissue delivery while still leaving a smooth surface on the repair site. Advantageously, use of the delivery device 156 allows delivery of the tissue fragments to a repair site without direct human contact with the fragments. However, in an alternative example of the delivery device 556, shown in FIG. 7C, the handle 557 of the delivery device 556 may be provided with an access door 559 allowing direct access to the tissue fragments, if desired.

As shown in FIG. 8A, a manual actuator 162, such as a thumb roller, may be provided on a surface of the handle 157 of the delivery device 156 for one-handed delivery of the tissue fragments to the repair site. In examples, as the actuator 162 is rotated, gear teeth 166 of an integral pinion gear 164 engage with corresponding teeth 168 on a surface of the plunger 158, causing the plunger 158 to move axially within the channel 160. In alternative examples, not shown, the interface between the actuator 162 and the plunger 158 could be a frictional engagement. In further examples, shown in FIG. 8B, limiting the loss of tissue fragments around the actuator 162 can be accomplished by preventing the rotation of the actuator 162 until mated with the plunger 158, and/or smoothing the gear teeth 166 in one area B, while still allowing full rotation of the actuator 162 (FIG. 8B).

Figure 9A:
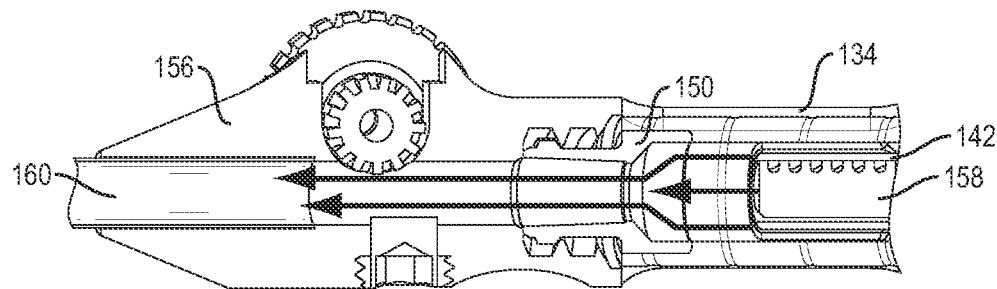
FIGS. 9A-C and FIGS. 11A-C are detailed views of the control mechanism between the plunger and the compressor of FIG. 7B.
Figure 9B:
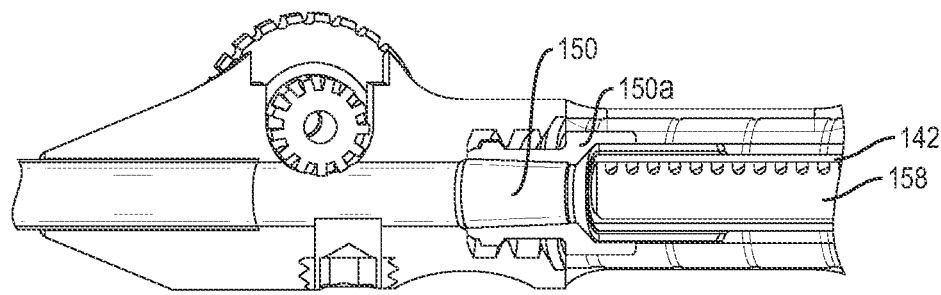
Figure 9C:
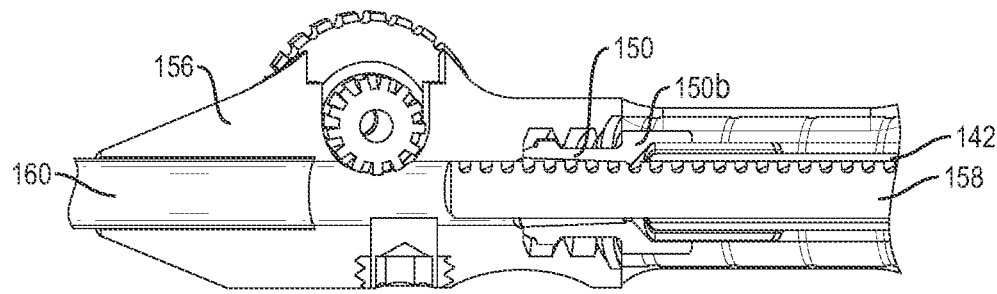

Turning now to FIG. 9A, when inserted through the compressor 142, the plunger 158 and the compressor 142 advance together through the housing 134 to push the tissue fragments into the channel 160 of the delivery device 156. The lip 150 now acts as a funnel to facilitate the flow of the tissue fragments into the channel 160. As the plunger 158 and the compressor 142 are advanced together, the compressor 142 is prevented from further advancement by the first portion 150a of the lip 150 (FIG. 9B). Once the compressor 142 is stopped by the lip 150, a mechanism allows the plunger 158 to advance through the second portion 150b of the lip 150 and into the channel 160 of the delivery device 156 (FIG. 9C). One example of the mechanism is described below with regard to FIGS. 11A-C. However, other suitable mechanisms for controlling this relative motion between the compressor 142 and the plunger 158 through the housing 134 are contemplated by this disclosure.

Figure 10A:
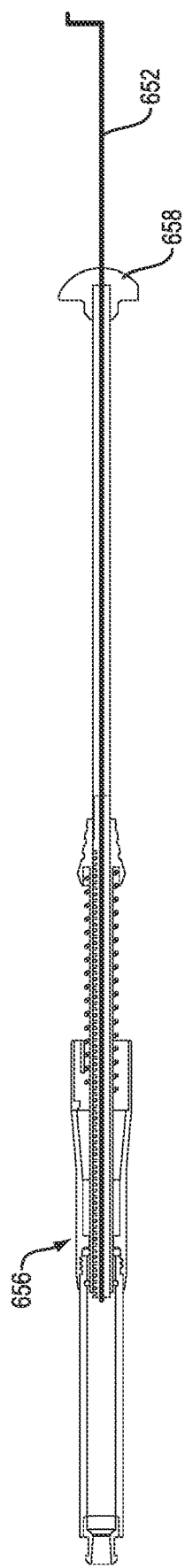
FIGS. 10A and 10B illustrate alternative examples of the mixing elements of FIG. 6A.
Figure 10B:
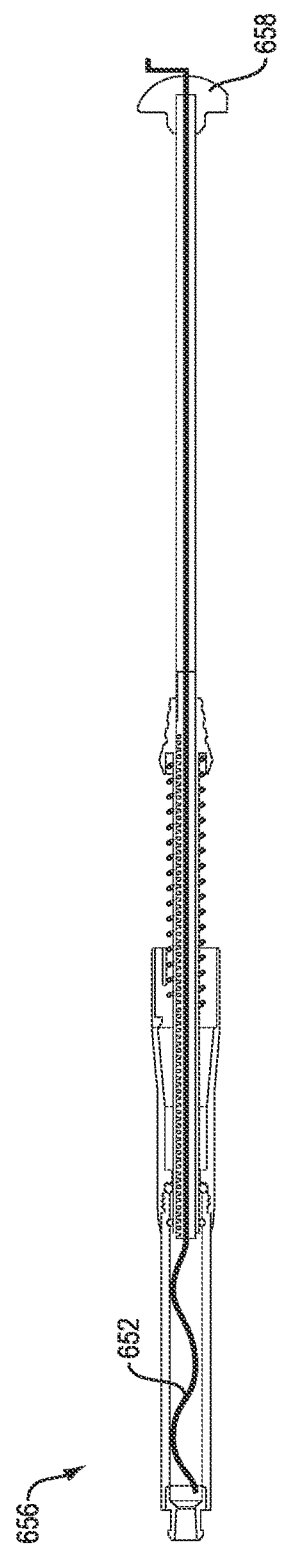

Alternative examples of the plunger 658 of this disclosure can incorporate mixing wires 652 within the plunger 658, as shown in FIGS. 10A and 10B. For example, the plunger 658 may be configured for the passage of a deformable mixing wire 652. The wire 652 is configured to be rotated and/or advanced within the delivery device 656 to further mix the contents of the delivery device 656 before delivery to the repair site.

Figure 11A:
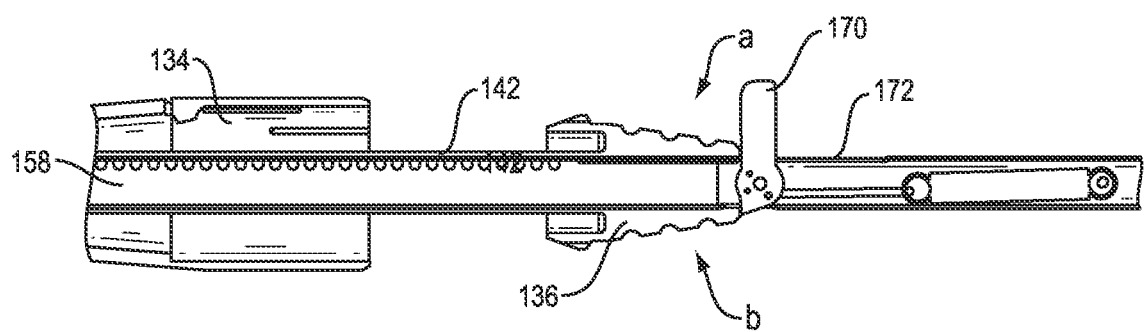
Figure 11B:
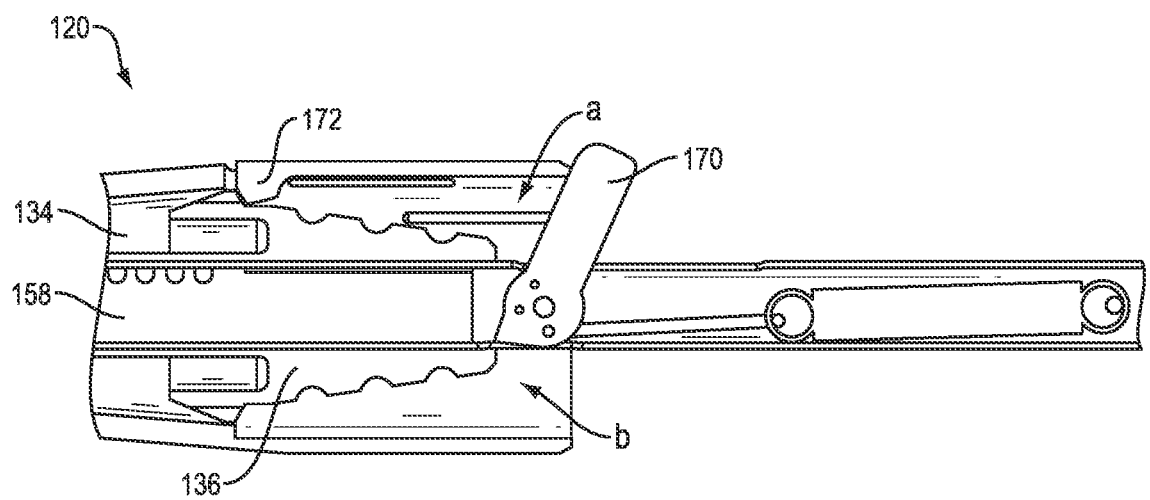
Figure 11C:
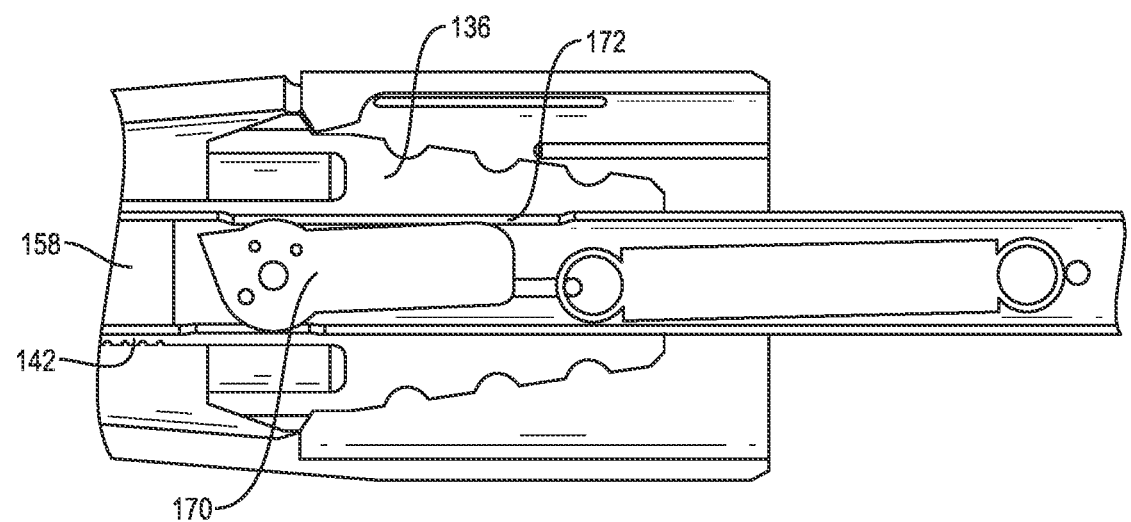

Further details regarding the interface between the compressor 142 and the plunger 158 are shown in FIGS. 11A-C. In order for the compressor 142 and the plunger 158 to move together through the housing 134, a mechanism is required to join them temporarily. In examples, the mechanism is a cam lever 170 extending from an interior of the plunger 158 through a slot 172 in the outer surface of the plunger 158. As shown in FIG. 11A, the cam lever 170 initially pushes against the inlet 136 at both points "a" and "b". As the inlet 136 and the plunger 158 are advanced through the housing 134, the cam lever 170 eventually comes into contact with a stationary feature (i.e., the distal end of the housing 134) and, with further advancement, begins to pivot, first lifting off of point "a" and then disengaging with point "b" (FIG. 11B). As the plunger 158 continues to advance, the cam lever 170 rotates to a horizontal position within the plunger 158, allowing the plunger 158 to continue advancing while leaving the compressor 142 in place (FIG. 11C). In alternative examples (not shown), a rotary motion of the plunger 158 relative to the compressor 142 could lock and unlock the plunger 158 and the compressor 142.

Figure 12A:
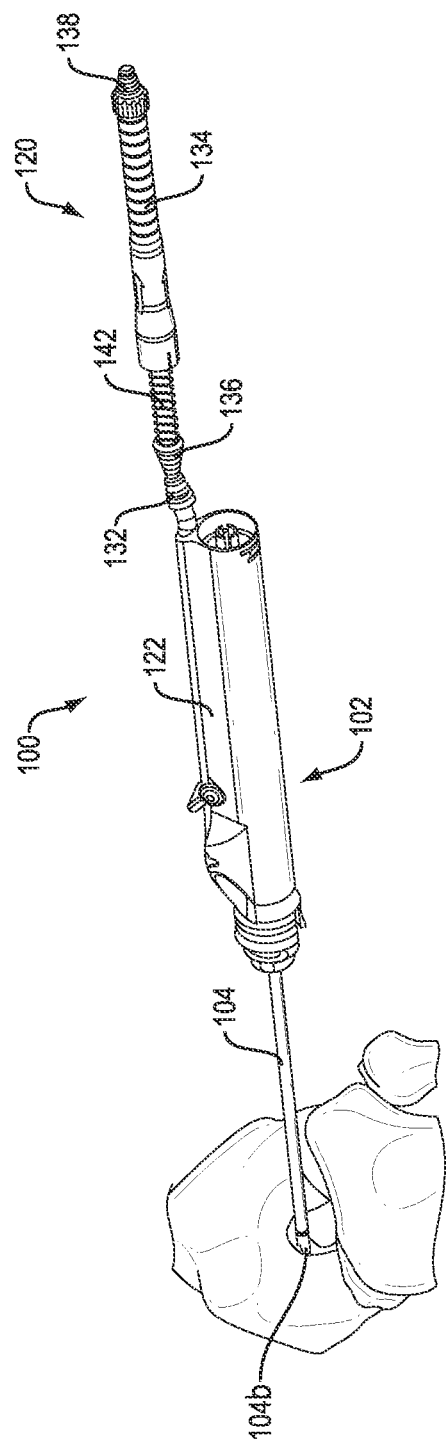
FIGS. 12A and 12B illustrate an exemplary method of using the tissue collection and delivery device of FIG. 7A.

Turning now to FIG. 12A, in operation, the resection system 102 of the tissue collection assembly 100 is brought into contact with a donor site and the operator cuts a desired amount of donor tissue from the site using the cutting end 104b. The vacuum source (not shown) aspirates fluid and the cut tissue through the shaft 104 and the handpiece 122 to the filter assembly 120. During aspiration, the fluid and cut tissue pass over the filter 140 (FIG. 4A) within the housing 134 where tissue fragments are isolated and/or retained on the outer surface of the filter 140. In examples, following aspiration of the fluid and cut tissue, the inlet 136 of the compressor 142 may be closed off using, for example, a valve, stop, plug, or other suitable device. The compressor 142 may then be advanced within the housing 134 to compress the tissue fragments within the housing 134 for measurement of the volume of the fragments. Aspiration of the fluid and cut tissue may be repeated until a desired volume of tissue fragments is reached, at which point the filter assembly 120 is removed from the resection system 102. The outlet 138 and the filter 140 are then removed from the housing 134, causing the lip 150 (FIG. 5A) to shear the tissue fragments from the outer surface of the filter 140. Optionally, a syringe or other instrument (not shown) containing a biocompatible agent is coupled to the housing 134, for example, by a Luer lock or other suitable connection in the housing 134. The agent is then injected into the housing 134 to mix with the tissue fragments. In examples, deformable wires 152 attached to the compressor 142 (FIG. 6A) may be rotated via rotation of the compressor 142 relative to the housing 134 to mix the tissue fragments and the agent to promote even distribution of the tissue fragments within the agent.

Figure 12B:
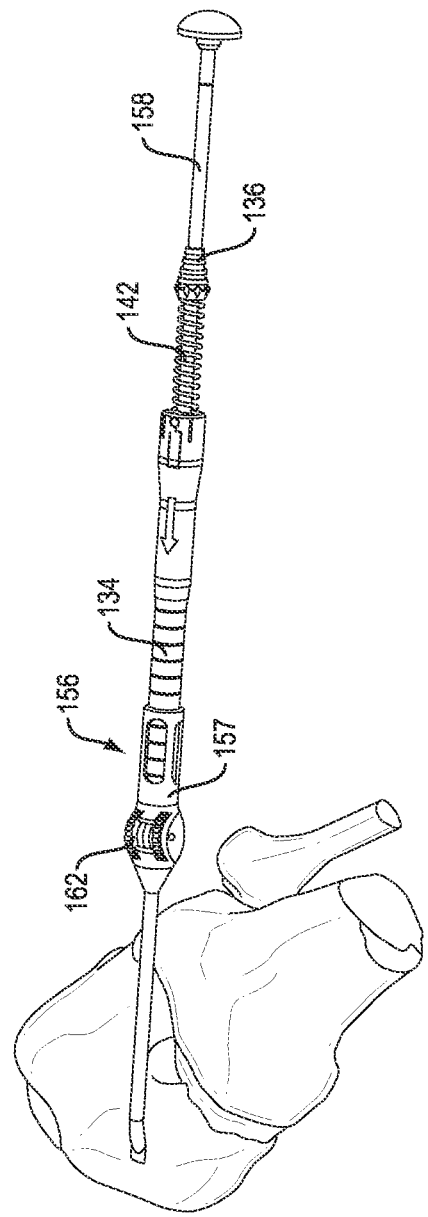

As shown in FIG. 12B, once the desired mixture is collected within the housing 134, the operator inserts the plunger 158 of the delivery device 156 into the inlet 136 of the compressor 142 and advances the plunger 158 and the compressor 142 together until the compressor 142 is prevented from further advancement within the housing 134. The compressor 142 may be latched into this position as the plunger 158 continues to travel past the region of the actuator 162. The operator then manually actuates the actuator 162 on the handle 157 to advance the plunger 158 through the delivery device 156 for controlled application of the tissue and agent mixture to the repair site. Alternatively, the mixture can be placed onto a tissue scaffold or used for further processing.

Figure 13:
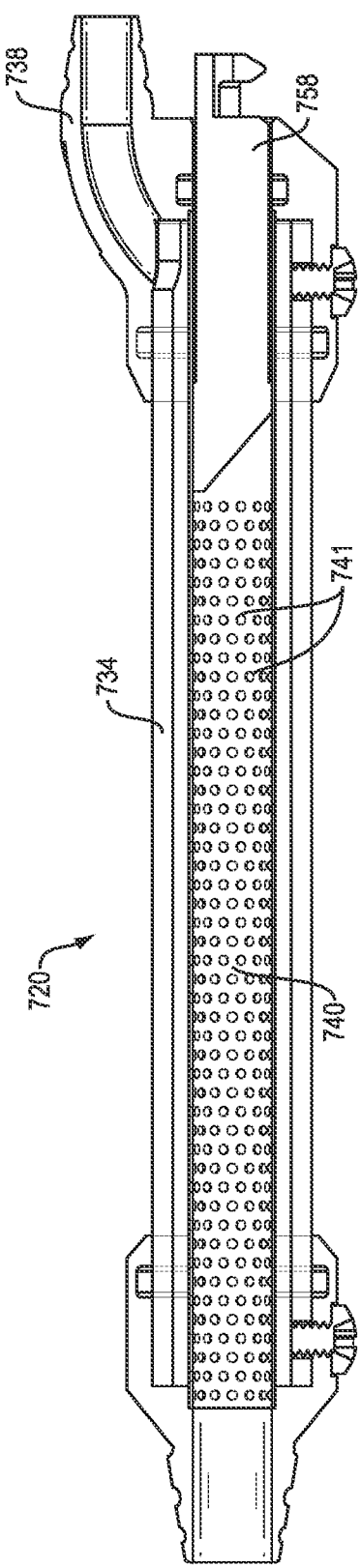
FIG. 13 illustrates an alternative example of the filter of FIG. 4A.

An alternative example of the filter assembly 720 is shown in FIG. 13. In the example of FIG. 13, suction is applied to the housing 734 through an offset outlet 738 providing fluid flow about the outer surface of the filter 740. As the suction is applied, fluid flowing through holes 741 in communication with the interior of the filter 740 causes the tissue fragments to be collected about the inner surface of the filter 740. In examples, a size of the holes 741 is selected to be smaller than a pre-selected size of the tissue fragments. The filter 740 of FIG. 13 may furthermore be configured for the passage of a syringe-type plunger 758 through an interior of the filter 740 to deliver the tissue fragments to the repair site.

In other examples, the filter 840 may be removeably disposed within the hub 824 of the blade 803, as shown in FIGS. 14A and 14B. In FIG. 14A, as suction S is applied, the filter 840 collects tissue fragments F on an exterior surface of the filter 840. In FIG. 14B, as suction S is applied, the filter 840 collects tissue fragments F on an interior surface of the filter 840. Optional joints 890 extend between the filter 840 and the cutting end 804b of the blade 803 for facilitating removal of the filter 840 from the blade 803.

Figure 15A:
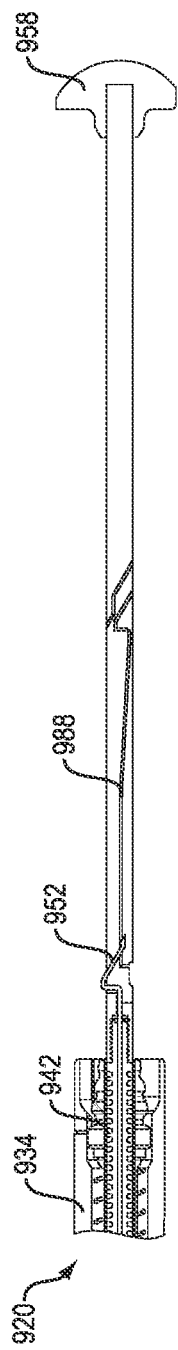
FIGS. 15A-C illustrate another example of the mixing elements of FIGS. 10A-C and the control mechanism of FIGS. 9A-C.
Figure 15B:
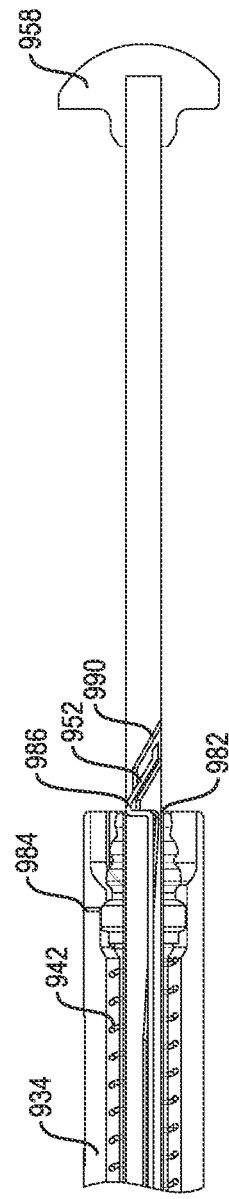
Figure 15C:
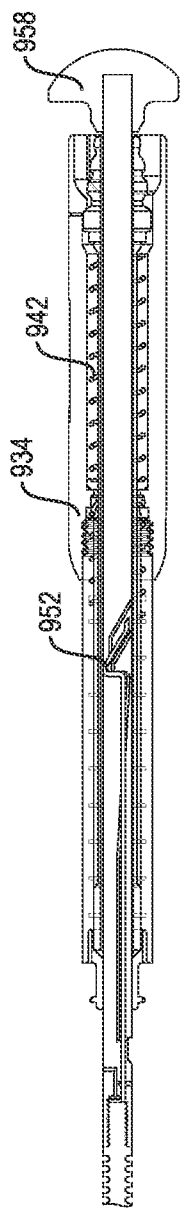

FIGS. 15A-C illustrate another example of a mixing wire 952 incorporated into the plunger 958. FIG. 15A shows the wire 952 housed within a track 988 of the plunger 958 as the plunger 958 is inserted through the compressor 942 within the housing 934 of the filter assembly 920. In FIG. 15A, the wire 952 is exposed beyond the distal end of the plunger 958 and can be used to mix the tissue fragments F with the biocompatible agent. As the plunger 958 advances through the compressor 942, the plunger 958 pushes the compressor 942 and the wire 952 together through the housing 934. As shown in FIG. 15B, when the plunger 958 is moved distally along the full length of the housing 934, the compressor 942 engages a latch 984 in the housing 934, preventing the compressor 942 from moving proximally. In addition, a bent portion 986 of wire 952 interferes with the compressor 942. As the plunger 958 continues to move distally, the plunger 958 covers the wire 952 until the wire 952 bottoms out at the end of the track 988 on the surface 982 of the plunger 958. At this stage, the distal end of the plunger 958 and wire 952 are substantially flush. The plunger 958 and the wire 952 continue to advance together within the housing 934 while the compressor 942 stays locked within the housing 934 (FIG. 15C).

The assemblies and devices described herein may be considered disposable, although they may also be reused upon sterilization, such as by gamma irradiation, ethylene oxide, formalin, hydrogen peroxide, or sodium hypochlorite. The filters and syringes discussed herein may be commercially obtained. In examples, the assemblies and devices, and their respective component parts, may be made of plastic, metal, or other suitable materials.

While the disclosure has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

What is claimed is:

1. A tissue collection assembly comprising:
 a handpiece having a proximal end, a distal end, and a passageway therethrough;
 a cannulated shaft attached to the distal end of the handpiece in fluid communication with the passageway, a distal end of the shaft configured to receive tissue fragments; and
 a filter assembly removeably attached to the proximal end of the handpiece in fluid communication with the cannulated shaft via a tube extending from the proximal end of the handpiece such that a distal end of the filter assembly is spaced apart from the proximal end of the handpiece, the filter assembly comprising:
 a housing allowing direct visualization of an internal volume of the housing; and
 a filter disposed within the internal volume of the housing for collecting the tissue fragments on a surface of the filter.

2. The tissue collection assembly of claim 1, further comprising a compressor extendable through the internal volume of the housing for compressing the tissue fragments.

3. The tissue collection assembly of claim 2, wherein the handpiece further comprises rigid tubing and a barb in fluid communication with the filter assembly.

4. The tissue collection assembly of claim 3, wherein the compressor comprises an inlet for removeable attachment to the barb.

5. The tissue collection assembly of claim 1, wherein the housing comprises a removeable outlet for attachment to a vacuum source.

6. The tissue collection assembly of claim 5, wherein the filter is coupled to the outlet such that the filter and the outlet are removeable from the housing simultaneously.

7. The tissue collection assembly of claim 1, wherein the housing further comprises a shearing member slidably disposed around the filter for removing the tissue fragments from the filter.

8. The tissue collection assembly of claim 1, further comprising a flexible shield adjacent the distal end of the shaft.

9. The tissue collection assembly of claim 1, wherein the handpiece is a motorized drive unit.

10. The tissue collection assembly of claim 1, wherein the assembly further includes a finger-engageable lever on a surface of the handpiece to control flow of the fragments through the passageway of the handpiece.

11. The tissue collection assembly of claim 1, wherein the handpiece comprises at least one internal structure to prevent contamination of the tissue fragments by the handpiece.

12. The tissue collection assembly of claim 11, wherein the at least one internal structure is a flow diverter.

13. The tissue collection assembly of claim 11, wherein the at least one internal structure is a sleeve integrated with the passageway of the handpiece.

14. The tissue collection assembly of claim 1, wherein the filter is a hollow, tubular filter, and the surface of the filter comprises holes in communication with an interior of the filter.

15. The tissue collection assembly of claim 1, wherein the filter assembly is coupleable with a delivery device to deliver the tissue fragments to a repair site.

16. The tissue collection assembly of claim 1, wherein the tissue fragments are selected from one of cartilage, bone, fat, meniscus, tendon, and ligament tissue fragments.

\* \* \* \* \*